United States Patent [19]

Zondler et al.

[11] Patent Number: 4,767,443
[45] Date of Patent: Aug. 30, 1988

[54] ANTIFUNGAL AND ANTIBACTERIAL DIAZINE DERIVATIVES COMPOSITIONS, INTERMEDIATES, AND METHOD OF USE THEREFOR

[75] Inventors: Helmut Zondler, Bottmingen, Switzerland; Wolfgang Eckhardt, Lörrach, Fed. Rep. of Germany; Robert Nyfeler, Basel, Switzerland

[73] Assignee: Ciba-Geigy Corporation, Ardsley, N.Y.

[21] Appl. No.: 775,972

[22] Filed: Sep. 13, 1985

[30] Foreign Application Priority Data

Sep. 20, 1984 [CH] Switzerland .......................... 4496/84
Aug. 8, 1985 [CH] Switzerland .......................... 3405/85

[51] Int. Cl.$^4$ ..................... A61K 43/54; C07D 239/42
[52] U.S. Cl. ........................................... 71/90; 71/90; 71/92; 544/60; 544/96; 544/122; 544/229; 544/295; 544/296; 544/322
[58] Field of Search ............... 544/229, 122, 322, 320, 544/333, 335, 60, 96, 295, 296; 71/92, 90; 514/256

[56] References Cited

U.S. PATENT DOCUMENTS 4,315,931 2/1982 Scharwaecher et al. ............ 544/322

OTHER PUBLICATIONS

American Heritage Dictionary, 1982, Houghton Mifflin Co., Boston, MA, p. 793.

*Primary Examiner*—Mary C. Lee
*Assistant Examiner*—J. G. Mullins
*Attorney, Agent, or Firm*—Edward McC. Roberts; Meredith C. Findlay

[57] ABSTRACT

There are described novel, microbicidally active 5-(arylmethylimino)-pyrimidines of the formula I

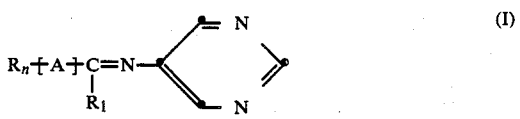

wherein $R_n$-$\{A\}$- is an unsubstituted or substituted phenyl, naphthyl, biphenyl, phenoxyphenyl or phenylthiophenyl, and $R_1$ is an ether, thioether or amino function, these substances being produced according to the invention by substitution of the halogen atom in the claimed intermediates of the formula II

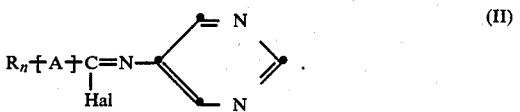

The use of these substances in plant protection, and also further important intermediates, are likewise described.

26 Claims, No Drawings

ANTIFUNGAL AND ANTIBACTERIAL DIAZINE DERIVATIVES COMPOSITIONS, INTERMEDIATES, AND METHOD OF USE THEREFOR

The present invention relates to novel 5-(arylmethylimino)-pyrimidines of the following formula I. The invention relates also to the production of these substances, as well as to compositions which contain as active ingredient at least one of these compounds. It relates moreover to the production of the compositions, and to the use of the active ingredients or of the compositions for controlling harmful microorganisms, particularly fungi and bacteria which damage plants. Furthermore, the invention relates to important intermediates of the formulae II and VI defined in the following.

The compounds according to the invention are those of the general formula I

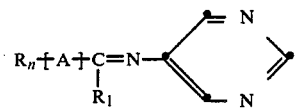

wherein
A is phenyl, naphthyl, biphenyl, phenoxyphenyl or phenylthiophenyl,
R is halogen, cyano, nitro, $C_1$–$C_4$-alkyl, $C_1$–$C_4$-alkoxycarbonyl, tris($C_1$–$C_4$-alkoxy)silyl, hydroxyl, $C_1$–$C_4$-alkoxy, $C_1$–$C_4$-haloalkoxy, $C_1$–$C_4$-haloalkyl or di($C_1$–$C_4$-alkyl)amino,
n is 0, 1, 2, 3, 4 or 5,
$R_1$ is one of the groups $OR_2$, $SR_2$ or $N(R_3)(R_4)$, in which
$R_2$ is $C_1$–$C_8$-alkyl, $C_3$–$C_8$-alkenyl, $C_3$–$C_8$-alkynyl, or a $C_1$–$C_8$-alkyl group monosubstituted by R, or a radical from the group comprising phenyl, phenalkyl($C_1$–$C_4$), $C_3$–$C_7$-cycloalkyl and furfuryl, which is unsubstituted or mono- to trisubstituted by R, and
$R_3$ and $R_4$ independently of one another are each hydrogen or $C_1$–$C_4$-alkyl, or together with the amine nitrogen form a saturated, five- or six-membered heterocycle which contains as hetero atom either just the amine nitrogen or a further hetero atom N, O or S.

By the term 'alkyl' itself or alkyl as a constituent of another substituent, such as alkoxy, haloalkyl, haloalkoxy, and so forth, are meant, depending on the given number of carbon atoms, for example the following straight-chain or branched-chain groups: methyl, ethyl, propyl, butyl, pentyl, hexyl, heptyl, octyl, and the like, and isomers thereof, for example: isopropyl, isobutyl, tertbutyl, isopentyl, and so forth. Halogen and halo represent fluorine, chlorine, bromine or iodine. Haloalkyl is accordingly a mono-to perhalogenated alkyl group, for example: $CHCl_2$, $CH_2F$, $CCl_3$, $CH_2Cl$, $CHF_2$, $CHFCH_3$, $CH_2CH_2Br$, $C_2Cl_5$, $CH_2Br$, $CHBrCl$, and so forth, preferably $CF_3$. Alkenyl is for example propenyl-(1), allyl, butenyl-(1), butenyl-(2) or butenyl-(3), as well as chains having several double bonds. $C_3$–$C_7$-cycloalkyl is optionally cyclopropyl, methylcyclopropyl, cyclobutyl, cyclopentyl, cyclohexyl or cycloheptyl. Alkynyl is for example: propionyl-(2), propargyl, butynyl-(1), butynyl-(2), and so forth, preferably propargyl. When the group $—N(R_3)(R_4)$ is a saturated five-or six-membered heterocycle having N as the hetero atom, preferred heterocycles are: pyrrolidine, piperazine, piperidine, perhydrothiazine, morpholine, oxazolidine, thiazolidine, imidazolidine and pyrazoline. Naphthyl represents α-and β-naphthyl. Phenoxyphenyl is (o-phenoxy)phenyl, (m-phenoxy)phenyl and (p-phenoxy)phenyl. Phenylthiophenyl is (o-phenylthio)phenyl, (m-phenylthio)phenyl and (p-phenylthio)phenyl. Likewise in biphenyl the second phenyl group can occupy the ortho-, meta- or para- position. Naphthyl, phenoxyphenyl, phenylthiophenyl and biphenyl can be substituted in both rings.

The compounds of the formula I can be used in agriculture or in related fields in a preventive and curative manner for controlling phytopathogenic microorganisms, such as fungi. The active ingredients of the formula I according to the invention are characterised, within broad limits of applied concentrations, by a high level of microbicidal activity, a wide range of action and low phytotoxicity, and they can be applied without difficulty, particularly in the agricultural field.

The following groups of active ingredients are preferred by virtue of their pronounced microbicidal activity, particularly phytofungicidal activity.

Group I'; Compounds of the formula I wherein A is phenyl, naphthyl, biphenyl, phenoxyphenyl or phenylthiophenyl, R is halogen, cyano, nitro, $C_1$–$C_4$-alkyl, $C_1$–$C_4$-alkoxy, $C_1$–$C_4$-haloalkoxy, $C_1$–$C_4$-haloalkyl or di($C_1$–$C_4$-alkyl)amino, n is 0, 1, 2, 3, 4 or 5, $R_1$ is one of the groups $OR_2$, $SR_2$ or $N(R_3)(R_4)$, in which $R_2$ is $C_1$–$C_8$-alkyl, $C_3$–$C_8$-alkenyl, $C_3$–$C_8$-alkynyl, or a radical from the group comprising phenyl, benzyl, $C_3$–$C_7$-cycloalkyl and furfuryl, which is unsubstituted or mono–to trisubstituted by R, and $R_3$ and $R_4$ independently of one another are each hydrogen or $C_1$–$C_4$-alkyl, or together with the amine nitrogen form a saturated, five- or six-membered heterocycle containing as hetero atom either just the amine nitrogen or a further hetero atom.

Group I-A: Compounds of the formula I wherein A is phenyl, R is hydroxyl, halogen, cyano, methyl, ethyl, methoxycarbonyl, ethoxycarbonyl, methoxy, ethoxy, $CF_3$, trimethoxysilyl, $C_1$–$C_2$-haloalkoxy, $N(CH_3)_2$ or $N(C_2H_5)_2$, n is 1, 2 or 3, $R_1$ is one of the groups $OR_2$ or $SR_2$, in which $R_2$ is $C_1$–$C_8$-alkyl, $C_3$–$C_8$-alkenyl, $C_3$–$C_8$-alkynyl, or a $C_1$–$C_4$-alkyl group which is monosubstituted by hydroxyl, halogen, cyano, methoxycarbonyl, ethoxycarbonyl, methoxy, ethoxy, trimethoxysilyl, triethoxysilyl, $N(CH_3)_2$ or $N(C_2H_5)_2$, or is a radical from the group comprising phenyl, phenethyl, benzyl, $C_5$–$C_6$-cycloalkyl and furfuryl, which is unsubstituted or mono- to trisubstituted by halogen, cyano, methyl, ethyl, methoxy, ethoxy, $CF_3$, $C_1$–$C_2$-haloalkoxy or $N(C_1$–$C_2$-alkyl)$_2$.

Group Ia: Compounds of the formula I wherein A is phenyl, R is halogen, cyano, methyl, ethyl, methoxy, ethoxy, $CF_3$, $C_1$–$C_2$-haloalkoxy, $N(CH_3)_2$ or $N(C_2H_5)_2$, n is 1, 2 or 3, $R_1$ is one of the groups $OR_2$ or $SR_2$, in which $R_2$ is $C_1$–$C_8$-alkyl, $C_3$–$C_8$-alkenyl, $C_3$–$C_8$-alkynyl, or a radical from the group comprising phenyl, benzyl, $C_5$–$C_6$-cycloalkyl and furfuryl, which is unsubstituted or mono- to trisubstituted by halogen, cyano, methyl, ethyl, methoxy, ethoxy, $CF_3$, $C_1$–$C_2$-haloalkoxy or $N(C_1$–$C_2$-alkyl)$_2$.

Group Ib: Compounds of the formula I wherein A is phenyl, R is fluorine, chlorine, bromine, methyl, me-

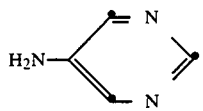

(IV)

is N-acylated, preferably in the presence of a base, with an acid halide, preferably with the chloride or bromide of the formula V

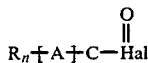

(V)

to a compound of the formula VI

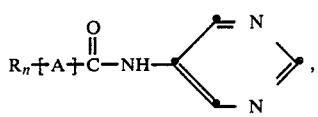

(VI)

and this is then halogenated, in a manner known per se (for example with $SOCl_2$, $PBr_5$, $PCl_5$, N-bromosuccinimide, and so forth) to a compound of the formula II. In the formulae V and VI, the substituents $R_n$ and A have the meanings defined under the formula I, and Hal is halogen, preferably chlorine or bromine. The reaction of (IV) with (V) to give (VI) is performed under the conditions described for the reaction of (II) with (III) to obtain (I).

Compounds of the formula I can be produced, applying a second production variant, by using also the compound of the formula VI as starting material, converting this by halogenation (for example with $SOCl_2$) into the halide of the formula II (chloride), and subsequently reacting II in situ, according to the invention, to obtain I. This single-vessel process likewise forms subject matter of this invention since the intermediate II occurs therein intermediately and, if desired, can be isolated from the reaction medium. The compounds of the formula VI are thus direct precursors in the production of the compounds of the formula I. They are novel and are moreover themselves microbicidally active. They exhibit, inter alia, a very good phytofungicidal action, and can be used for example in the same area of indications as that applying in the case of the final products of the formula I. The compounds of the formula VI constitute a part of the present invention. 5-Aminopyrimidine is known from the literature (cf. Whittaker, J. Chem. Soc. 1951, p. 1568). Likewise known are the acid halides of the formula V; or they can be produced by methods known per se, or by processes analogous to those for obtaining the known representatives.

Typical representatives of the formula II, within the scope of the present invention, are for example the following compounds:

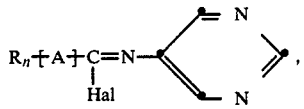

(II)

this list of compounds having no limiting character: (temperatures are given in degrees Centigrade)

| Comp. No. | $R_n$[-A-] | Hal | |
|---|---|---|---|
| 1 | $C_6H_3Cl_2(2,4)$ | Cl | hydrochloride m.p. 132–136° (decomp.) |
| 2 | $C_6H_3Cl_2(2,4)$ | Br | |
| 3 | $C_6H_4Cl(4)$ | Cl | hydrochloride m.p. 136–138° (decomp.) |
| 4 | $C_6H_4Cl(4)$ | Br | |
| 5 | $C_6H_4F(4)$ | Cl | |
| 6 | $C_6H_4F(4)$ | Br | |
| 7 | $C_6H_4F(3)$ | Cl | m.p. 81–82° |
| 8 | $C_6H_4F(3)$ | Br | |
| 9 | $C_6H_4F(2)$ | Cl | |
| 10 | $C_6H_4F(2)$ | Br | |
| 11 | $C_6H_4Cl(2)$ | Cl | |
| 12 | $C_6H_4Cl(2)$ | Br | |
| 13 | $C_6H_4Br(4)$ | Cl | |
| 14 | $C_6H_4Br(4)$ | Br | |
| 15 | $C_6H_3Br_2(2,5)$ | Cl | |
| 16 | $C_6H_3Br_2(2,5)$ | Br | |
| 17 | $C_6H_3Cl_2(2,6)$ | Cl | |
| 18 | $C_6H_3Cl_2(2,6)$ | Br | |
| 19 | $C_6H_3F_2(2,6)$ | Cl | |
| 20 | $C_6H_3F_2(2,6)$ | Br | |
| 21 | $C_6H_4J(2)$ | Cl | |
| 22 | $C_6H_4J(2)$ | Br | |
| 23 | $C_6H_4J(3)$ | Cl | |
| 24 | $C_6H_3J_2(2,3)$ | Cl | |
| 25 | $C_6H_3J_2(3,4)$ | Cl | |
| 26 | $C_6H_4CH_3(4)$ | Cl | |
| 27 | $C_6H_4CH_3(4)$ | Br | |
| 28 | $C_6H_3(CH_3)_2(2,4)$ | Cl | |
| 29 | $C_6H_3(CH_3)_2(3,4)$ | Cl | |
| 30 | $C_6H_4CF_3(4)$ | Cl | |
| 31 | $C_6H_4CH_3(3)$ | Cl | |
| 32 | $C_6H_3CH_3(2)NO_2(4)$ | Cl | |
| 33 | $C_6H_2CH_3(3)(NO_2)_2(3,5)$ | Cl | |
| 34 | $C_6H_3CH_3(5)NO_2(2)$ | Cl | |
| 35 | $C_6H_3(CH_3)_2(2,3)$ | Cl | |
| 36 | $C_6H_2J_3(2,3,5)$ | Cl | |
| 37 | $C_6H_4[C(CH_3)_3](4)$ | Cl | |
| 38 | $C_6H_4[N(CH_3)_2](4)$ | Cl | |
| 39 | $C_6H_4[N(CH_3)_2](3)$ | Cl | |
| 40 | $C_6H_4OCH_3(3)$ | Cl | |
| 41 | $C_6H_4OCH_3(2)$ | Cl | |
| 42 | $C_6H_3(OCH_3)_2(3,5)$ | Cl | |
| 43 | $C_6H_3(OCH_3)_2(3,4)$ | Cl | |
| 44 | $C_6H_3(OCH_3)(2,4)$ | Cl | |
| 45 | $C_6H_4C_6H_5(4)$ | Cl | |
| 46 | $C_6H_4C_6H_5(4)$ | Br | |
| 47 | $C_6H_4(CH_2C_6H_5)(4)$ | Cl | |
| 48 | $C_6H_4(CH_2C_6H_5)(4)$ | Br | |
| 49 | α-Naphthyl | Cl | |
| 50 | α-Naphthyl | Br | |
| 51 | β-Naphthyl | Cl | |
| 51a | $C_6H_4Cl(2)$, Br(4) | Cl | oil |
| 51b | $C_6H_4F(2)$, Cl(4) | Cl | oil, | and also compounds of the formula II, wherein $R_n$—A— is

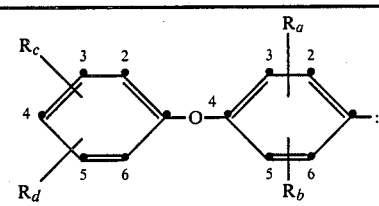

| Comp. No. | $R_a$ | $R_b$ | $R_c$ | $R_d$ | Hal | |
|---|---|---|---|---|---|---|
| 52 | H | H | H | H | Cl | oil |
| 53 | H | H | H | H | Br | |
| 54 | 2-Cl | H | H | H | Cl | |
| 55 | 2-Cl | H | H | H | Br | |
| 56 | 2-CH₃ | H | H | H | Cl | |
| 57 | 2-CH₃ | H | H | H | Br | |
| 58 | H | H | 4-Cl | H | Cl | oil |
| 59 | H | H | 4-Cl | H | Br | |
| 60 | H | H | 4-CH₃ | H | Cl | |
| 61 | H | H | 4-CH₃ | H | Br | |
| 62 | 2-Cl | H | 4-Cl | H | Cl | |
| 63 | 2-Cl | H | 4-Cl | H | Br | |
| 64 | 2-CH₃ | H | 4-CH₃ | H | Cl | |

-continued

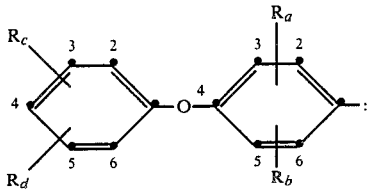

| Comp. No. | $R_a$ | $R_b$ | $R_c$ | $R_d$ | Hal |
|---|---|---|---|---|---|
| 65 | 2-CH$_3$ | H | 4-CH$_3$ | H | Br |
| 66 | 2-Cl | H | 4-CH$_3$ | H | Cl |
| 67 | 2-Cl | H | 4-CH$_3$ | H | Br |
| 68 | 2-CH$_3$ | H | 4-Cl | H | Cl |
| 69 | 2-CH$_3$ | H | 4-Cl | H | Br |
| 70 | 2-Cl | 3-Cl | 4-Cl | 2-Cl | Cl |
| 71 | 2-Cl | 3-Cl | 4-CH$_3$ | H | Cl |
| 72 | 2-CH$_3$ | H | 4-Cl | 2-Cl | Cl |
| 73 | H | H | 4-CF$_3$ | H | Cl |
| 74 | H | H | 4-OCH$_3$ | H | Cl |

Typical representatives of compounds of the formula VI

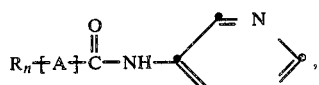 (VI)

within the scope of the rpesent invention are for example:

| Comp. No. | $R_n\text{-}A\text{-}$ | Physical constants [°C.] |
|---|---|---|
| 75 | C$_6$H$_4$NO$_2$(4) | m.p. 193–194° |
| 76 | C$_6$H$_3$Cl$_2$(2,4) | m.p. 139–140° |
| 77 | C$_6$H$_4$Cl(4) | m.p. 177–179° |
| 78 | C$_6$H$_4$F(4) | m.p. 148–150° |
| 79 | C$_6$H$_4$F(3) | m.p. 162–163° |
| 80 | C$_6$H$_4$F(2) | m.p. 125–126° |
| 81 | C$_6$H$_4$Cl(2) | |
| 82 | C$_6$H$_4$Br(4) | m.p. 194–196° |
| 83 | C$_6$H$_3$Br$_2$(2,5) | |
| 84 | C$_6$H$_3$Cl$_2$(2,6) | |
| 85 | C$_6$H$_3$F$_2$(2,6) | |
| 86 | C$_6$H$_4$J(2) | resin |
| 87 | C$_6$H$_4$J(3) | |
| 88 | C$_6$H$_3$J$_2$(2,3) | |
| 89 | C$_6$H$_4$CH$_3$(4) | m.p. 150–153° |
| 90 | C$_6$H$_3$(CH$_3$)$_2$(2,4) | |
| 91 | C$_6$H$_3$(CH$_3$)$_2$(3,4) | |
| 92 | C$_6$H$_4$CF$_3$(4) | |
| 93 | C$_6$H$_4$CH$_3$(3) | |
| 94 | C$_6$H$_3$CH$_3$(2)NO$_2$(4) | |
| 95 | C$_6$H$_2$CH$_3$(3)(NO$_2$)$_2$(3,5) | |
| 96 | C$_6$H$_3$CH$_3$(5)NO$_2$(2) | |
| 97 | C$_6$H$_3$(CH$_3$)$_2$(2,3) | |
| 98 | C$_6$H$_2$J$_3$(2,3,5) | |
| 99 | C$_6$H$_4$[C(CH$_3$)$_3$](4) | m.p. 214–216° |
| 100 | C$_6$H$_4$[N(CH$_3$)$_2$](3) | |
| 101 | C$_6$H$_4$OCH$_3$(3) | |
| 102 | C$_6$H$_3$(OCH$_3$)$_2$(3,5) | |
| 103 | C$_6$H$_3$(OCH$_3$)$_2$(3,4) | |
| 104 | C$_6$H$_3$(OCH$_3$)$_2$(2,4) | |
| 105 | C$_6$H$_4$C$_6$H$_5$(4) | |
| 106 | C$_6$H$_4$(CH$_2$C$_6$H$_5$)(4) | |
| 107 | α-naphthyl | |
| 108 | β-naphthyl | |
| 108a | C$_6$H$_2$(OCH$_3$)$_3$(3,4,5) | m.p. 167–169° |
| 108b | C$_6$H$_5$ | m.p. 140–143° |
| 108c | C$_6$H$_4$NH$_2$(4) | m.p. 247–248° |
| 108d | C$_6$H$_4$OCH$_3$(4) | m.p. 217–218° |
| 108e | C$_6$H$_4$CF$_3$(2) | m.p. 154–156° |
| 108f | C$_6$H$_4$F(2), Cl(4) | m.p. 138–141° |
| 108g | C$_6$H$_4$Cl(2), Br(4) | m.p. 145–150° | and also compounds of the formula VI wherein $R_n$—A— is

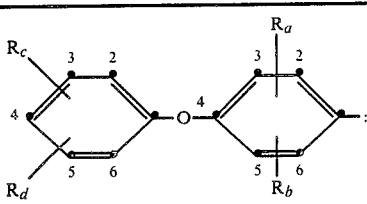

| Comp. No. | $R_a$ | $R_b$ | $R_c$ | $R_d$ | Physical constants |
|---|---|---|---|---|---|
| 109 | H | H | H | H | m.p. 155–158° |
| 110 | 2-Cl | H | H | H | |
| 111 | 2-CH$_3$ | H | H | H | |
| 112 | H | H | 4-Cl | H | m.p. 196–199° |
| 113 | H | H | 4-CH$_3$ | H | |
| 114 | 2-Cl | H | 4-Cl | H | m.p. 211–212° |
| 115 | 2-CH$_3$ | H | 4-CH$_3$ | H | |
| 116 | 2-Cl | H | 4-CH$_3$ | H | |
| 117 | 2-CH$_3$ | H | 4-Cl | H | m.p. 157–159° |
| 118 | 2-Cl | 3-Cl | 4-Cl | 2-Cl | |
| 119 | 2-Cl | 3-Cl | 4-CH$_3$ | H | |
| 120 | 2-CH$_3$ | H | 4-Cl | 2-Cl | |
| 121 | H | H | 4-CH$_3$ | 2-Cl | |
| 122 | H | H | 4-CF$_3$ | H | |
| 123 | H | H | 4-OCH$_3$ | H | |
| 124 | 2-OCH$_3$ | H | H | H | |
| 125 | 2-OCH$_3$ | H | 4-OCH$_3$ | H | |
| 126 | H | H | 4-OCH$_3$ | 2-OCH$_3$ | |

Analogously to the C=C double bond, the C=N double bond in the compounds of the formula I, and also in the intermediates of the formula II, leads to varying geometrical isomers:

Compounds of the formula I

Compounds of the formula I

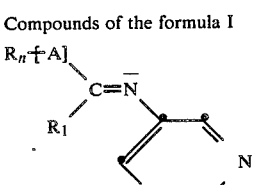 (I)

syn-R$_1$ or anti-$R_n$-[A]-; (trans form)

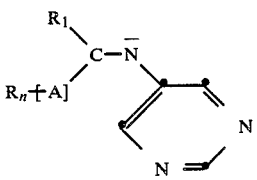

syn-$R_n$-[A]- or anti- R$_1$ (cis form)

Compounds of the formula II

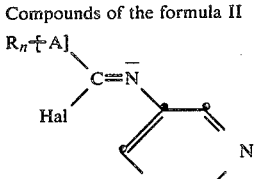

syn-Hal or anti-$R_n$-[A]-; (trans form)

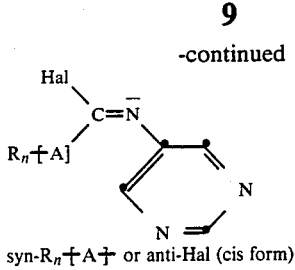

syn-R$_n$─┼─A─┼─ or anti-Hal (cis form)

There is generally formed in the production of compounds of the formulae I and II a mixture of the cis and trans forms, the thermodynamically more favourable form being preferentially formed. The substances can be used without separation of the isomers in plant protection. The use of the pure isomers can however result in an intensification of the action.

The invention accordingly relates to all isomeric compounds of the formula I in the pure form or in any chosen numerical ratio with respect to one another.

The production process for compounds of the formula I in the described variants thereof forms a part of this invention.

It has been established that compounds of the formula I surprisingly exhibit, for practical requirements, a very favourable microbicidal spectrum against phytopathogenic fungi and bacteria. The compounds have very advantageous curative, preventive and systemic properties, and can be used for the protection of cultivated plants. The microorganisms occurring on plants or on parts of plants (fruit, blossom, foliage, stalks, tubers or roots) of various cultivated crops can be inhibited or destroyed with the active substances of the formula I, and also parts of plants subsequently growing remain preserved from such microorganisms.

The active substances of the formula I are effective against the phytopathogenic fungi belonging to the following classes: Ascomycetes (for example Venturia, Podosphaera, Erysiphe, Monilinia and Uncinula); Basidiomycetes (for example the species Hemileia, Rhizoctonia and Puccinia); Fungi imperfecti (for example Botrytis, Helminthosporium, Fusarium, Septoria, Cercospora and Alternaria). Furthermore, the compounds of the formula I have a systemic action. They can also be used as dressing agents for the treatment of seed (fruits, tubers or grain), and of plant cuttings to protect them from fungus infections, and also against phytopathogenic fungi occurring in the soil. The active substances according to the invention are distinguished also by a particularly high tolerance to cultivated plants.

The present invention thus relates also to microbicidal compositions, and to the use of the compounds of the formula I for controlling phytopathogenic microorganisms, especially fungi which damage plants, and for preventing an infestation of plants.

In addition, the present invention relates also to the production of agrochemical compositions, whereby the active substance is intimately mixed together with one or more carrier materials described herein. Also included is a process for treating plants, which comprises the application of the compounds of the formula I or of the novel compositions.

Within the scope of this invention, target crops with respect to the range of indications disclosed herein include for example the following species of cultivated plants: cereals: (wheat, barley, rye, oats, rice, sorghum and related cereals); beet: (sugar beet and fodder beet): pomaceous fruit, stone fruit and soft fruit: (apples, pears, plums, peaches, almonds, cherries, strawberries, raspberries and blackberries); legumes: (beans, lentils, peas and soya-bean); oil plants: (rape, mustard, poppy, olives, sunflowers, coco, castor-oil plants, cocoa and groundnuts); Cucurbitacea: (pumpkins, cucumbers and melons); fibre plants: (cotton, flax, hemp and jute); citrus fruits: (oranges, lemons, grapefruit and mandarins); varieties of vegetables: (spinach, lettuce, asparagus, varieties of cabbage, carrots, onions, tomatoes, potatoes and paprika); laurel plants: (avocada, cinnamon and camphor); or plants such as maize, tobacco, nuts, coffee, sugar beet, tea, grapevines, hops, bananas and natural rubber plants; and also ornamental plants: (flowers, shrubs, deciduous trees and coniferous trees, such as conifers). This list constitutes no limitation.

Active substances of the formula I are customarily used in the form of compositions, and can be applied, simultaneously or successively, with further active substances to the area or plants to be treated. These further active substances can be fertilisers, trace-element agents or other preparations influencing plant growth. They can however also be selective herbicides, insecticides, fungicides, bactericides, nematicides or molluscicides, or mixtures of several of these preparations, optionally together with carriers commonly used in formulation practice, tensides or other additives facilitating application.

Suitable carriers and additives can be solid or liquid and they correspond to the substances customarily employed in formulation practice, for example natural or regenerated mineral substances, solvents, dispersing agents, wetting agents, adhesives, thickeners, binders or fertilisers.

A preferred method of applying an active substance of the formula I is application to the foliage (leaf application) or to the soil (soil application). The compounds of the formula I can however be applied also to the seed grains (coating), either by soaking the grains in a liquid preparation of the active substance, or coating them with a solid preparation.

The compounds of the formula I are used either in an unmodified form or preferably together with auxiliaries customarily employed in formulation practice, and are thus processed in a known manner for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions. Favourable applied amounts are in general between 50 g and 5 kg of active substance (AS) per hectare, preferably between 100 g and 2 kg of AS per hectare, and in particular between 100 g and 600 g of AS per hectare.

Suitable solvents are: hydrocarbons, for example xylene mixtures, hexane or cyclohexane, alcohols and glycols, as well as ethers and esters thereof, such as ethanol, ethylene glycol, ethylene glycol monomethyl- or -ethyl ethers, ketones, such as cyclohexanone, polar solvents, such as N-methyl-2-pyrrolidone, dimethyl sulfoxide or dimethylformamide, and also optionally epoxidised vegetable oils, such as epoxidised coconut oil or soybean oil; or water.

The solid carriers used, for example for dusts and dispersible powders, are as a rule natural mineral fillers, such as calcite, talcum. kaolin, montmorillonite or attapulgite. To improve the physical properties, it is also possible to use highly dispersed silicic acid or highly dispersed absorbent polymers. Particularly advantageous additives facilitating application are moreover natural or synthetic phospholipides from the series of cephalins and lecithins, for example: phosphatidyl ethanolamine, phosphatidyl serine, phosphatidyl glycerol and lysolecithin.

Depending on the nature of the active ingredient of the formula I to be formulated, suitable surface-active compounds are nonionic, cationic and/or anionic tensides having good emulsifying, dispersing and wetting properties. By 'tensides' are also meant mixtures of tensides.

Suitable anionic tensides can be for example water-soluble soaps (fatty acid salts).

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups.

The tensides customarily used in formulation practice are described, inter alia, in the following publications:

"Mc Cutcheon's Detergents and Emulsifiers Annual", MC Publishing Corp., Ridgewood, New Jersey, 1981;

Dr. Helmut Stache "Tensid-Taschenbuch" (Tenside Handbook) Carl Hanser Verlag, Munich/Vienna, 1981.

The agrochemical preparations contain as a rule 0.1 to 99%, particularly 0.1 to 95%, of active ingredient of the formula I, 99.9 to 1%, especially 99.8 to 5%, of a solid or liquid additive, and 0 to 25%, in particular 0.1 to 25%, of a tenside.

Whereas commercial products are preferably in the form of concentrated compositions, the compositions employed by the end-user are as a rule diluted.

The compositions can also contain further additives, such as stabilisers, antifoaming agents, viscosity regulators, binders and adhesives, as well as fertilisers or other active ingredients for obtaining special effects.

Agrochemical compositions of the types described herein likewise form part of the present invention.

The following Examples serve to further illustrate the invention without limiting the scope thereof. Percentage values and 'parts' relate to weight. There are also used the following symbols: h=hour; d=day; min=minute; RT=room temperature; N=normality; abs.=absolutely anhydrous; DMSO=dimethyl sulfoxide; DMF=dimethylformamide. Pressure values are given in millibar mb, or bar b. $C_6H_5$ always denotes a phenyl group. A substituted phenyl group, for example ortho-, para-dichlorophenyl, is accordingly abbreviated to $C_6H_3Cl_2(2,4)$.

PRODUCTION EXAMPLES

EXAMPLE P1

Production of

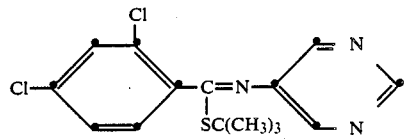

5-[2,4-Dichlorobenzyl-C-(tert-butylthio)imino]-pyrimidine (a) Preparation of intermediate

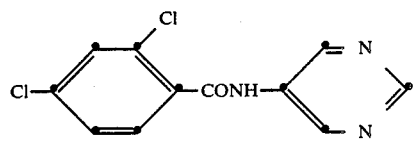

A solution of 8.62 g (0.041 mol) of 2,4-dichlorobenzoyl chloride in 10 ml of tetrahydrofuran is added dropwise at 50° C. to a solution of 3.26 g (0.0343 mol) of 5-aminopyrimidine in 20 ml of tetrahydrofuran and 20 ml of pyridine, in the course of which pyridine hydrochloride precipitates. Water is added, and extraction is performed with the addition of 20 ml of concentrated HCl at pH 1 with chloroform. After the drying of the extract with $Na_2SO_4$, there are obtained, on concentration by evaporation, 10.9 g of crude product, which is recrystallised from 50 ml of toluene and 10 ml of ethyl acetate; yield 2.58 g (28.1% of theory); m.p. 139°–141° C. When the filtrate is concentrated by evaporation, a further 2.49 g (27.1% of theory) of product, m.p. 137°–139° C., crystallise out. The filtrate is concentrated by evaporation, and the residue is chromatographed through a silica gel column (eluant: 2 parts of ethyl acetate/1 part of hexane) to obtain a further 2.05 g (22.3% of theory) of substance.

(b) Production of N-(5-pyrimidyl)-2,4-dichlorobenzimide chloride

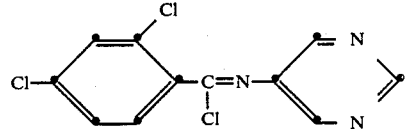

10.7 g (0.04 mol) of N-(2,4-dichlorobenzoyl)-5-aminopyrimidine are gradually heated with 10 g of phosphorus pentachloride to 120° C., in the course of which, with the evolution of HCl, there is formed a solution. After one hour, the solution is diluted with 1 ml of toluene and 15 ml of cyclohexane, and the whole is allowed to cool with stirring, during which there crystallises out N-(5-pyrimidyl)2,4-dichlorobenzimide chloride as hydrochloride, which is filtered off with suction, washed with cyclohexane, and dried in a desiccator over P₂O₅. The yield is 5.5 g; m.p. 132°-136° C. (decomposition).

(c) Production of final product 10.6 g (0.0395 mol) of N-(2,4-dichlorobenzoyl)-5-aminopyrimidine are refluxed with 30 ml of thionyl chloride for 2 hours. Concentration of the solution in vacuo in a rotary evaporator yields, as intermediate, N-(5-pyrimidyl)2,4-dichlorobenzimide chloride which, for further reaction, is immediately dissolved in 100 ml of pyridine, and the solution with 8.8 ml of tert-butyl-mercaptan is held at 100° C. for 3 hours. The solution is afterwards poured into 700 ml of ice-water, and extraction is performed with ethyl acetate. After washing of the extract with water, drying with Na₂SO₄ and concentration by evaporation, the yield is 10.8 g of crude product, which is purified by means of a silica gel column (eluant: 2 parts of petroleum ether/1 part of ethyl acetate). There are thus obtained 8.4 g (62.5% of theory) of substance which, after recrystallisation from a mixture of toluene and cyclohexane, has a melting point of 108°-109° C.

EXAMPLE P2

Production of

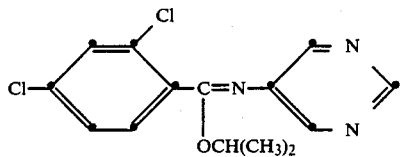

To a solution of 2.9 ml of 2-propanol (0.037 mol) in 30 ml of tetrahydrofuran are added portionwise 2.1 g of 55% sodium hydride in oil, in the course of which Na-isopropylate precipitates. There is then added dropwise at −10° C., with cooling, a solution of 0.025 mol of crude N-(5-pyrimidyl)-2,4-dichlorobenzim(de chloride in 30 ml of tetrahydrofuran (for production cf. Example P1c). The reaction mixture is subsequently poured at room temperature into ice water and is extracted with ethyl acetate. The organic phase is dried with Na₂SO₄ and concentrated by evaporation to obtain a crude product which, by means of a chromatography column, is purified through silica gel with a mixture of 3 parts of hexane and 1 part of ethyl acetate. There are thus obtained 4.8 g of substance which, after recrystallisation, yields 3.9 g of pure product having a melting point of 85°-86° C.

EXAMPLE P3

Production of

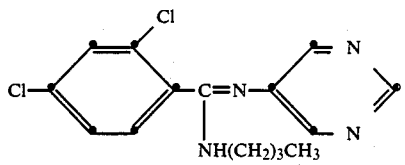

0.02 mol of crude N-(5-pyrimidyl)-2,4-dichlorobenzimide chloride (for production cf. Example P1c) is dissolved in 30 ml of dioxane, and the solution with 5.9 ml of n-butyl amine is heated at 80° C. for 1 hour. After cooling, the reaction mixture is extracted with methylene chloride and water, the organic phase is dried with Na₂SO₄ and then concentrated by evaporation. Purification of the crude product (7.4 g) through a chromatography column with silica gel, with the use of ethyl acetate as the eluant, yields 5.7 g of pure substance in the form of oil, $n_D^{40}=1.5810$.

By procedures analogous to those described, there are obtained also the compounds of the formula I listed below:

TABLE 1

Compounds of the formula

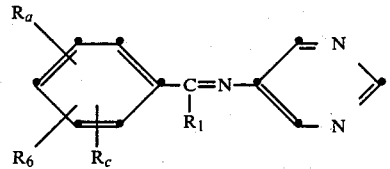

| Comp. No. | $R_a$ | $R_b$ | $R_c$ | $R_1$ | Physical constants [°C.] |
|---|---|---|---|---|---|
| 1.1 | 4-Cl | 2-Cl | H | SC(CH₃)₃ | m.p. 108-109° |
| 1.2 | 4-Cl | 2-Cl | H | SCH₃ | m.p. 85-87° |
| 1.3 | 4-Cl | 2-Cl | H | SCH(CH₃)₂ | m.p. 76-78° |
| 1.4 | 4-Cl | 2-Cl | H | SCH₂CH₂CH₃ | $n_D^{40}$ 1.6123 |
| 1.5 | 4-Cl | 2-Cl | H | S(CH₂)₉CH₃ | |
| 1.6 | 4-Cl | 2-Cl | H | SCH₂CH₂N(C₂H₅)₂ | |
| 1.7 | 4-Cl | 2-Cl | H | SCH₂–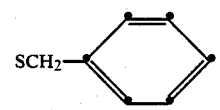 | $n_D^{48}$ 1.6465 |
| 1.8 | 4-Cl | 2-Cl | H | SCH₂CH=CH₂ | |
| 1.9 | 4-Cl | 2-Cl | H | 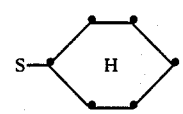 | m.p. 86-88° |

TABLE 1-continued

Compounds of the formula

[Structure: Ra, Rb, Rc, R6 substituted phenyl-C(R1)=N-pyrimidine]

| Comp. No. | R_a | R_b | R_c | R_1 | Physical constants [°C.] |
|---|---|---|---|---|---|
| 1.10 | 4-Cl | 2-Cl | H | S—phenyl | |
| 1.11 | 4-Cl | 2-Cl | H | $OCH_3$ | $n_D^{24}$ 1.5965 |
| 1.12 | 4-Cl | 2-Cl | H | $OCH(CH_3)_2$ | m.p. 85–86° |
| 1.13 | 4-Cl | 2-Cl | H | $OC(CH_3)_3$ | m.p. 103–104° |
| 1.14 | 4-Cl | 2-Cl | H | $OCH_2CF_3$ | m.p. 96–98° |
| 1.15 | 4-Cl | 2-Cl | H | $OCH_2CH_2CN$ | |
| 1.16 | 4-Cl | 2-Cl | H | $OCH_2CH_2NO_2$ | |
| 1.17 | 4-Cl | H | H | $SC(CH_3)_3$ | m.p. 129–130° |
| 1.18 | 4-Cl | H | H | $SCH(CH_3)_2$ | |
| 1.19 | 4-Cl | H | H | $SCH_3$ | |
| 1.20 | 4-Cl | H | H | $SCH_2CH(CH_3)_2$ | |
| 1.21 | 4-Cl | H | H | $SCH_2CH_2OH$ | |
| 1.22 | 4-F | H | H | $SCH_3$ | |
| 1.23 | 4-F | H | H | $SC(CH_3)_3$ | m.p. 102–103° |
| 1.24 | 4-F | H | H | $SCH(CH_3)_2$ | $n_D^{28}$ 1.5910 |
| 1.25 | 3-F | H | H | $SC(CH_3)_3$ | m.p. 76° |
| 1.26 | 3-F | H | H | $SC_2H_5$ | $n_D^{25}$ 1.6075 |
| 1.27 | 2-F | H | H | $SCH(CH_3)_2$ | |
| 1.28 | 2-Cl | H | H | $SCH(CH_3)_2$ | |
| 1.29 | 4-Br | H | H | $SC(CH_3)_3$ | m.p. 120–121° |
| 1.30 | 4-Br | H | H | $SCH(C_3H_5)(C_3H_7)$ | $n_D^{26}$ 1.6065 |
| 1.31 | 2-Br | 5-Br | H | $SC(CH_3)_3$ | |
| 1.32 | 2-Cl | 5-Cl | H | $SC(CH_3)_3$ | |
| 1.33 | 2-Cl | 6-Cl | H | $SCH_3$ | |
| 1.34 | 2-F | 6-F | H | $SC_2H_5$ | |
| 1.35 | 2-Cl | 6-F | H | $SC(CH_3)_3$ | |
| 1.36 | 2-J | H | H | $SC_3H_7$ | |
| 1.37 | 3-J | H | H | $SC_2H_5$ | |
| 1.38 | 2-J | 3-J | 5-J | $SC_3H_7(n)$ | |
| 1.39 | 3-J | 4-J | 5-J | $SC_3H_7(n)$ | |
| 1.40 | 3-J | H | H | $SC_4H_9(n)$ | |
| 1.41 | 2-Cl | 4-Cl | H | $OCH_2C\equiv CH$ | oil |
| 1.42 | 2-$CH_3$ | 4-Cl | H | O—phenyl—$NO_2$ | |
| 1.43 | 4-$CH_3$ | H | H | $OCH(CH_3)_2$ | $n_D^{24}$ 1.5618 |
| 1.44 | 4-$CH_3$ | H | H | $SC_2H_5$ | $n_D^{24}$ 1.6183 |
| 1.45 | 4-$CH_3$ | H | H | S—phenyl—H | $n_D^{23}$ 1.6080 |
| 1.46 | 4-$CH_3$ | 2-$CH_3$ | H | $N(CH_3)_2$ | |
| 1.47 | 4-$CH_3$ | 3-$CH_3$ | H | $OCH_2CH_2OCH_3$ | |
| 1.48 | 4-$CF_3$ | H | H | $SC_3H_7(n)$ | |
| 1.49 | 3-$CF_3$ | H | H | S—phenyl—$OCH_3$ | |

TABLE 1-continued

Compounds of the formula

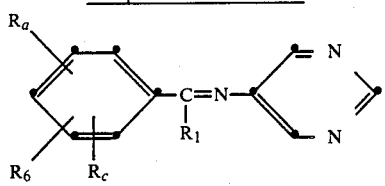

| Comp. No. | $R_a$ | $R_b$ | $R_c$ | $R_1$ | Physical constants [°C.] |
|---|---|---|---|---|---|
| 1.50 | 2-CF$_3$ | H | H | OCH$_3$ | |
| 1.51 | 2-CH$_3$ | 4-CH$_3$ | 6-CH$_3$ | SC$_3$H$_7$(n) | |
| 1.52 | 3-CH$_3$ | H | H | OC$_2$H$_5$ | |
| 1.53 | 2-CH$_3$ | 3-NO$_2$ | 5-NO$_2$ | OCH$_3$ | |
| 1.54 | 3-CH$_3$ | 4-NO$_2$ | H | SCH(CH$_3$)$_2$ | |
| 1.55 | 5-CH$_3$ | 2-NO$_2$ | H | SCH$_3$ | |
| 1.56 | 2-CH$_3$ | H | H | OCH(CH$_3$)$_2$ | |
| 1.57 | 2-CH$_3$ | 3-CH$_3$ | H | S—⟨phenyl(H)(Cl)⟩ | |
| 1.58 | 2-CH$_3$ | 5-CH$_3$ | H | SCH$_2$CH$_2$N(CH$_3$)$_2$ | |
| 1.59 | 3-CH$_3$ | 5-CH$_3$ | H | S—⟨phenyl-OCH$_3$⟩ | |
| 1.60 | 4-C(CH$_3$)$_3$ | H | H | SCH(CH$_3$)$_2$ | m.p. 93-94° |
| 1.61 | 4-C(CH$_3$)$_3$ | H | H | OCH$_2$CH(CH$_3$)$_2$ | |
| 1.62 | 4-Cl | 3-NO$_2$ | 5-NO$_2$ | OCH$_3$ | |
| 1.63 | 4-CN | H | H | CH$_3$O—⟨phenyl-S⟩ | |
| 1.64 | 2-NO$_2$ | 4-NO$_2$ | H | N(C$_3$H$_7$)$_2$ | |
| 1.65 | 2-NO$_2$ | 4-NO$_2$ | H | OC$_3$H$_7$(n) | |
| 1.66 | 2-NO$_2$ | 4-NO$_2$ | H | SCH$_2$CH$_2$OH | |
| 1.67 | 3-NO$_2$ | 4-NO$_2$ | H | SCH$_2$—⟨dihydrofuran-O⟩ | |
| 1.68 | 3-NO$_2$ | 5-NO$_2$ | H | O(CH$_2$)$_9$CH$_3$ | |
| 1.69 | 4-NO$_2$ | H | H | SC(CH$_3$)$_3$ | |
| 1.70 | 4-NO$_2$ | H | H | SC$_4$H$_9$(n) | $n_D^{23}$ 1.6138 |
| 1.71 | 2-NO$_2$ | H | H | SCH(CH$_3$)(C$_2$H$_5$) | |
| 1.72 | 2-NO$_2$ | H | H | OCH$_3$ | |
| 1.73 | 3-NO$_2$ | H | H | SCH(CH$_3$)$_2$ | |
| 1.74 | 3-NO$_2$ | H | H | N(CH$_3$)$_2$ | |
| 1.75 | 4-N(CH$_3$)$_2$ | H | H | O—⟨phenyl⟩ | |
| 1.76 | 4-N(CH$_3$)$_2$ | H | H | S—⟨phenyl-F⟩ | |

TABLE 1-continued

Compounds of the formula

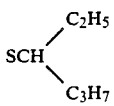

| Comp. No. | $R_a$ | $R_b$ | $R_c$ | $R_1$ | Physical constants [°C.] |
|---|---|---|---|---|---|
| 1.77 | 3-N(CH$_3$)$_2$ | H | H | SCH$_3$ | |
| 1.78 | 3-OCH$_3$ | 5-OCH$_3$ | H | SCH(CH$_3$)$_2$ | |
| 1.79 | 3-OCH$_3$ | 4-OCH$_3$ | H | SCH(C$_2$H$_5$)(C$_3$H$_7$) | |
| 1.80 | 2-OCH$_3$ | 4-OCH$_3$ | H | OC$_5$H$_{11}$(n) | |
| 1.81 | 2-OCH$_3$ | 6-OCH$_3$ | H | 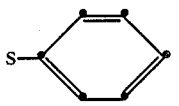 | |
| 1.82 | 2-OCH$_3$ | 3-OCH$_3$ | H | SCH$_3$ | |
| 1.83 | 2-OCH$_3$ | H | H | SC(CH$_3$)$_3$ | |
| 1.84 | 3-OCH$_3$ | H | H | SCH(CH$_3$)$_2$ | |
| 1.85 | 4-OCH$_3$ | H | H | SCH(CH$_3$)$_2$ | $n_D^{26}$ 1.6084 |
| 1.86 | 4-C$_6$H$_5$ | H | H | SC(CH$_3$)$_3$ | |
| 1.87 | 2-C$_6$H$_5$ | H | H | SC(CH$_3$)$_3$ | |
| 1.88 | 2-Cl | 4-Cl | H | OCH$_2$CH=CH$_2$ | $n_D^{40}$ 1.5830 |
| 1.89 | 4-Cl | 2-Cl | H | SCH$_2$CH(CH$_3$)$_2$ | resin |
| 1.90 | 4-Cl | H | H | S—C$_6$H$_4$CH$_3$(4) | m.p. 155–156° |
| 1.91 | 4-OCH$_3$ | H | H | SC(CH$_3$)$_3$ | m.p. 56–59° |
| 1.92 | 4-Cl | 2-Cl | H | SCH(C$_2$H$_5$)C$_3$H$_7$(n) | $n_D^{48}$ 1.5810 |
| 1.93 | 4-Cl | 2-Cl | H | 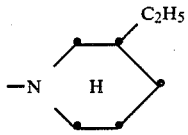 | $n_D^{48}$ 1.579 |
| 1.94 | 4-Cl | 2-Cl | H | O—C$_6$H$_4$CH$_3$(3) | m.p. 127–128° |
| 1.95 | 4-Cl | 2-Cl | H | N(C$_2$H$_5$)$_2$ | $n_D^{48}$ 1.5900 |
| 1.96 | 4-F | H | H | OCH$_2$CF$_3$ | m.p. 96–97° |
| 1.97 | 4-F | H | H | O—cyclohexyl | $n_D^{23}$ 1.5638 |
| 1.98 | 4-F | H | H | OCH$_2$CH$_2$CH$_3$ | m.p. 60–61° |
| 1.99 | 4-Cl | 2-Cl | H | OCH$_2$CH$_2$CH$_3$ | m.p. 59–61° |
| 1.100 | 4-Cl | 2-Cl | H | SC$_2$H$_5$ | $n_D^{26}$ 1.6284 |
| 1.101 | 4-Cl | 2-Cl | H | S(CH$_2$)$_3$CH$_3$ | $n_D^{24}$ 1.6087 |
| 1.102 | 4-Cl | 2-Cl | H | SCH$_2$CH$_2$N(CH$_3$)$_2$ | |
| 1.103 | 4-Cl | 2-Cl | H | SCH(CH$_3$)C$_2$H$_5$ | $n_D^{27}$ 1.6075 |
| 1.104 | 4-Cl | 2-Cl | H | SCH$_2$CH$_2$—C$_6$H$_5$ | |
| 1.105 | 4-Cl | 2-Cl | H | 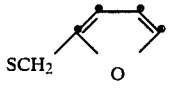 | |
| 1.106 | 4-Cl | 2-Cl | H | 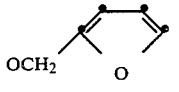 | |
| 1.107 | 4-Cl | 2-Cl | H | O—cyclohexyl | |
| 1.108 | 4-Cl | 2-Cl | H | NHC$_4$H$_9$(n) | $n_D^{40}$ 1.5810 |
| 1.109 | 4-Cl | 2-Cl | H | NHCH(CH$_3$)$_2$ | |
| 1.110 | 4-Cl | 2-Cl | H | NHC(CH$_3$)$_3$ | m.p. 153° |
| 1.111 | 4-Cl | 2-Cl | H | NH—cyclopropyl | |
| 1.112 | 4-Cl | 2-Cl | H | NH—cyclohexyl | |
| 1.113 | 4-CH$_3$ | H | H | OC(CH$_3$)$_3$ | |
| 1.114 | 4-CH$_3$ | H | H | SC(CH$_3$)$_3$ | m.p. 101–102° |
| 1.115 | 4-C(CH$_3$)$_3$ | H | H | SC(CH$_3$)$_3$ | m.p. 161–162° |
| 1.116 | 4-C(CH$_3$)$_3$ | H | H | OCH(CH$_3$)$_2$ | |
| 1.117 | 4-C(CH$_3$)$_3$ | H | H | SCH(C$_2$H$_5$)C$_3$H$_7$(n) | $n_D^{25}$ 1.5674 |

TABLE 1-continued

Compounds of the formula

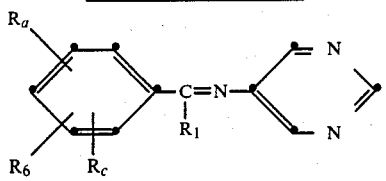

| Comp. No. | $R_a$ | $R_b$ | $R_c$ | $R_1$ | Physical constants [°C.] |
|---|---|---|---|---|---|
| 1.118 | 4-C(CH$_3$)$_3$ | H | H | OC(CH$_3$)$_3$ | |
| 1.119 | 4-C(CH$_3$)$_3$ | H | H | NHCH(CH$_3$)$_2$ | |
| 1.120 | 2-CF$_3$ | H | H | SC(CH$_3$)$_3$ | m.p. 81–83° |
| 1.121 | 3-OCH$_3$ | 4-OCH$_3$ | 5-OCH$_3$ | OC(CH$_3$)$_3$ | |
| 1.122 | 3-OCH$_3$ | 4-OCH$_3$ | 5-OCH$_3$ | SC$_2$H$_5$ | |
| 1.123 | 3-OCH$_3$ | 4-OCH$_3$ | 5-OCH$_3$ | SC(CH$_3$)$_3$ | m.p. 123–124° |
| 1.124 | 3-OCH$_3$ | 4-OCH$_3$ | 5-OCH$_3$ | SCH(C$_2$H$_5$)C$_3$H$_7$(n) | m.p. 70° |
| 1.125 | 3-N(CH$_3$)$_2$ | H | H | SC(CH$_3$)$_3$ | |
| 1.126 | 3-N(CH$_3$)$_2$ | H | H | OCH(CH$_3$)C$_2$H$_5$ | |
| 1.127 | 2-J | H | H | SC(CH$_3$)$_3$ | m.p. 126–127° |
| 1.128 | 4-Br | H | H | OCH(CH$_3$)$_2$ | m.p. 95–96° |
| 1.129 | 2-J | H | H | SC$_3$H$_7$(iso) | n$_D^{27}$ 1.6390 |
| 1.130 | 2-J | H | H | SC$_4$H$_9$(iso) | n$_D^{27}$ 1.6240 |
| 1.131 | 4-CN | H | H | SC$_4$H$_9$(tert.) | |
| 1.132 | 3-Cl | 5-Cl | H | SC$_3$H$_7$(iso) | |
| 1.133 | 3-Cl | 5-Cl | H | OC$_4$H$_9$(tert.) | |
| 1.134 | 3-Cl | 5-Cl | H | SC$_4$H$_9$(tert.) | |
| 1.135 | 3-Cl | 5-Cl | H | S—Cyclohexyl | |
| 1.136 | 3-Cl | 5-Cl | H | OCH$_2$CF$_3$ | |
| 1.137 | 4-F | H | H | SCH(C$_2$H$_5$)C$_3$H$_7$(n) | n$_D^{28}$ 1.5710 |
| 1.138 | 4-Cl | H | H | SC$_2$H$_5$ | |
| 1.139 | 4-Cl | H | H | SCH(C$_2$H$_5$)C$_3$H$_7$(n) | |
| 1.140 | 4-Cl | H | H | S—Cyclohexyl | |
| 1.141 | 4-Cl | H | H | OC$_4$H$_9$(tert.) | |
| 1.142 | 4-Cl | 2-Cl | H | SC(CH$_3$)$_2$C$_2$H$_5$ | m.p. 89° |
| 1.143 | 4-CH$_3$ | H | H | SCH(CH$_3$)$_2$ | m.p. 48–50° |
| 1.144 | 4-Cl | 2-Cl | H | SCH$_2$CH$_2$CH(CH$_3$)$_2$ | |
| 1.145 | 4-Cl | 2-Cl | H | SCH$_2$CHOH<br>\|<br>CH$_3$ | |
| 1.146 | 4-Cl | 2-Cl | H | SCH$_2$CH$_2$OC$_2$H$_5$ | |
| 1.147 | 4-Cl | 2-Cl | H | SCH$_2$CH$_2$CN | |
| 1.148 | 4-Cl | 2-Cl | H | S—cyclopentyl | |
| 1.149 | 4-Cl | 2-Cl | H | SCH$_2$COOCH$_3$ | |
| 1.150 | 4-Cl | 2-Cl | H | SCH$_2$CH$_2$Si(OC$_2$H$_5$)$_3$ | n$_D^{24}$ 1.5540 |
| 1.151 | 4-Cl | 2-Cl | H | SCH$_2$CH$_2$CH$_2$Si(OCH$_3$)$_3$ | |
| 1.152 | 4-Cl | 2-F | H | SC(CH$_3$)$_3$ | m.p. 101–103° |
| 1.153 | 4-Cl | 2-F | H | SCH(CH$_3$)$_2$ | m.p. 62–65° |
| 1.154 | 4-Cl | 2-F | H | SC$_3$H$_7$(n) | |
| 1.155 | 4-Cl | 2-F | H | SC$_4$H$_9$(n) | |
| 1.156 | 4-Cl | 2-F | H | S—Benzyl | m.p. 86–89° |
| 1.157 | 4-Cl | 2-F | H | S—C$_6$H$_4$Cl(4) | n$_D^{40}$ 1.6386 |
| 1.158 | 4-Cl | 2-F | H | O—C$_6$H$_4$Cl(4) | m.p. 111–123° |
| 1.159 | 4-Cl | 2-F | H | NHC$_4$H$_9$(sec) | wax |
| 1.160 | 4-Cl | 2-F | H | OC$_3$H$_7$(n) | |
| 1.161 | 4-Cl | 2-F | H | OC$_3$H$_7$(iso) | |
| 1.162 | 4-Cl | 2-F | H | SCH(C$_2$H$_5$)C$_3$H$_7$(n) | |
| 1.163 | 4-Cl | 2-F | H | OC$_4$H$_9$(tert.) | |
| 1.164 | 4-Cl | 2-Cl | H | N(CH$_3$)$_2$ | |
| 1.165 | 4-Cl | H | H | N(CH$_3$)$_2$ | |
| 1.166 | 4-Cl | H | H | (5-membered N–H ring) | |
| 1.167 | 4-Cl | H | H | (6-membered N–H ring) | |

TABLE 1-continued

Compounds of the formula

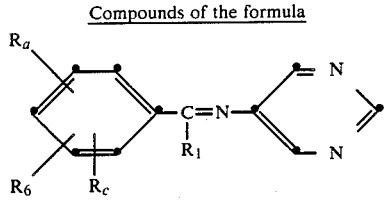

| Comp. No. | $R_a$ | $R_b$ | $R_c$ | $R_1$ | Physical constants [°C.] |
|---|---|---|---|---|---|
| 1.168 | 4-Cl | H | H | N–H, NH ring | |
| 1.169 | 4-Cl | H | H | N, O ring | |
| 1.170 | H | H | H | N–H ring | |
| 1.171 | 4-Cl | H | H | N, S ring | |
| 1.172 | H | H | H | N, O ring | |
| 1.173 | 4-Cl | H | H | N, S ring | |
| 1.174 | 2-Cl | 4-Cl | H | $OCH(CF_3)_2$ | |
| 1.175 | $4-C_6H_5$ | H | H | $SCH_3$ | |
| 1.176 | $4-C_6H_5$ | H | H | $SC_2H_5$ | |
| 1.177 | $4-C_6H_5$ | H | H | $SC_3H_7(n)$ | |
| 1.178 | $4-C_6H_5$ | H | H | $SC_3H_7(iso)$ | |
| 1.179 | $4-C_6H_5$ | H | H | $SC_4H_9(n)$ | |
| 1.180 | $4-C_6H_5$ | H | H | $SC_4H_9(iso)$ | |
| 1.181 | $4-C_6H_5$ | H | H | $SC_4H_9(sec)$ | |
| 1.182 | $4-C_6H_5$ | H | H | $OCH_3$ | |
| 1.183 | $4-C_6H_5$ | H | H | $OC_2H_5$ | |
| 1.184 | $4-C_6H_5$ | H | H | $OC_3H_7(n)$ | |
| 1.185 | $4-C_6H_5$ | H | H | $OC_3H_7(iso)$ | |
| 1.186 | $4-C_6H_5$ | H | H | $OC_4H_9(n)$ | |
| 1.187 | $4-C_6H_5$ | H | H | $OC_4H_9(iso)$ | |
| 1.188 | $4-C_6H_5$ | H | H | $OC_4H_9(sec)$ | |
| 1.189 | $4-C_6H_5$ | H | H | $OC_4H_9(tert.)$ | |
| 1.190 | $4-C_6H_5$ | H | H | $OCH_2CH=CH_2$ | |
| 1.191 | $4-C_6H_5$ | H | H | $OCH_2C\equiv CH$ | |
| 1.192 | $4-C_6H_5$ | H | H | $NHCH_3$ | |
| 1.193 | $4-C_6H_5$ | H | H | $NHC_3H_7(iso)$ | |
| 1.194 | $4-C_6H_5$ | H | H | $N(C_2H_5)_2$ | |
| 1.195 | $4-C_6H_5$ | H | H | N, O ring | |
| 1.196 | 2-Cl | H | H | $SC(CH_3)_3$ | |
| 1.197 | 2-Cl | H | H | $SC(CH_3)_2C_2H_5$ | |
| 1.198 | 2-Cl | H | H | $NHC(CH_3)_3$ | |
| 1.199 | 2-Cl | H | H | $OCH(CH_3)_2$ | |

TABLE 1-continued

Compounds of the formula

| Comp. No. | $R_a$ | $R_b$ | $R_c$ | $R_1$ | Physical constants [°C.] |
|---|---|---|---|---|---|
| 1.200 | 2-Cl | H | H | $OC(CH_3)_3$ | |
| 1.201 | 2-Cl | H | H | $NHCH(CH_3)_2$ | |
| 1.202 | 2-Cl | H | H | $OC_3H_7(n)$ | |
| 1.203 | 2-$CH_3$ | 4-$CH_3$ | H | $SCH(CH_3)_2$ | |
| 1.204 | 2-$CH_3$ | 4-$CH_3$ | H | $SC(CH_3)_2C_2H_5$ | |
| 1.205 | 2-$CH_3$ | 4-$CH_3$ | H | $OCH(CH_3)_2$ | |
| 1.206 | 2-$CH_3$ | 4-$CH_3$ | H | $NHCH(CH_3)_2$ | |
| 1.207 | 2-Cl | 5-Cl | H | $OCH(CH_3)C_2H_5$ | |
| 1.208 | 2-Cl | 5-Cl | H | $OCH(CH_3)_2$ | |
| 1.209 | 2-Cl | 5-Cl | H | $OC(CH_3)_3$ | |
| 1.210 | 2-Cl | 5-Cl | H | $SCH(CH_3)_2$ | |
| 1.211 | 2-Cl | 3-Cl | H | $OC_2H_5$ | |
| 1.212 | 2-Cl | 3-Cl | H | $OCH(CH_3)_2$ | |
| 1.213 | 2-Cl | 3-Cl | H | $NHCH(CH_3)_2$ | |
| 1.214 | 2-Cl | 3-Cl | H | $NHC(CH_3)_3$ | |
| 1.215 | 2-Cl | 3-Cl | H | $SC(CH_3)_3$ | |
| 1.216 | 2-Cl | 3-Cl | H | $SC(CH_3)_2C_2H_5$ | |
| 1.217 | 2-Cl | 3-Cl | H | $SCH(CH_3)C_2H_5$ | |
| 1.218 | 4-Cl | 2-F | H | $SCH_2CH=CH_2$ | $n_D^{40}$ 1.6107 |
| 1.219 | 4-Br | 2-Cl | H | $SC(CH_3)_3$ | oil |
| 1.220 | 4-Br | 2-Cl | H | $SCH(CH_3)_2$ | oil |
| 1.221 | 4-Br | 2-Cl | H | $SCH_2CH=CH_2$ | |
| 1.222 | 4-Br | 2-Cl | H | $SCH_2-C_6H_5$ | oil |
| 1.223 | 4-Br | 2-Cl | H | $S-C_6H_4(Cl)(4)$ | |
| 1.224 | 4-Br | 2-Cl | H | $O-C_6H_4(Cl)(4)$ | oil |
| 1.225 | 4-Br | 2-Cl | H | $NHCHC_2H_5$ with $CH_3$ substituent | |
| 1.226 | 4-Br | 2-Cl | H | $OC(CH_3)_3$ | oil |

TABLE 2

Compounds of the formula

| Comp. No. | $R_a$ | $R_b$ | $R_c$ | $R_d$ | $R_1$ | Physical constants [°C.] |
|---|---|---|---|---|---|---|
| 2.1 | H | H | H | H | $SC(CH_3)_3$ | m.p. 94–96° |
| 2.2 | H | H | H | H | $SCH_3$ | |
| 2.3 | 2-Cl | H | H | H | $OCH(CH_3)_2$ | |
| 2.4 | 2-Cl | H | H | H | $SC(CH_3)_3$ | |
| 2.5 | 2-$CH_3$ | H | H | H | $OCH_2CF_3$ | |
| 2.6 | 2-$CH_3$ | H | H | H | $OCH_3$ | |
| 2.7 | H | H | 4-Cl | H | $SC(CH_3)_3$ | m.p. 111–114° |
| 2.8 | H | H | 4-Cl | H | $SCH(CH_3)_2$ | oil |
| 2.9 | H | H | 4-$CH_3$ | H | $SCH_2CH_2CH_3$ | |
| 2.10 | H | H | 4-$CH_3$ | H | $OCH_2CF_3$ | |
| 2.11 | 2-Cl | H | 4-Cl | H | $OCH(CH_3)_2$ | m.p. 95° |
| 2.12 | 2-Cl | H | 4-Cl | H | $SC(CH_3)_2$ | m.p. 135–136° |
| 2.13 | 2-$CH_3$ | H | 4-$CH_3$ | H | $SCH(CH_3)_2$ | |
| 2.14 | 2-$CH_3$ | H | 4-$CH_3$ | H | $SCH_3$ | |
| 2.15 | 2-Cl | H | 4-$CH_3$ | H | $SC(CH_3)_3$ | |
| 2.16 | 2-Cl | H | 4-$CH_3$ | H | $OCH(CH_3)_2$ | |
| 2.17 | 2-$CH_3$ | H | 4-Cl | H | $OCH_3$ | |
| 2.18 | 2-$CH_3$ | H | 4-Cl | H | $SCH_2CH=CH_2$ | |
| 2.19 | 2-Cl | 3-Cl | 4-Cl | 2-Cl | S—phenyl | |
| 2.20 | 2-Cl | 3-Cl | 4-$CH_3$ | H | $OCH_2C\equiv CH$ | |
| 2.21 | 2-$CH_3$ | H | 4-Cl | 2-Cl | $S-C_6H_4F(4)$ | |
| 2.22 | H | H | H | 4-$CF_3$ | $SC(CH_3)_3$ | |

TABLE 2-continued

Compounds of the formula $$R_c\text{-phenyl-O-phenyl}(R_a,R_b)\text{-C}(R_1)=N\text{-[ring with 2 N]}$$

with $R_c, R_d$ on first phenyl and $R_a, R_b$ on second phenyl.

| Comp. No. | $R_a$ | $R_b$ | $R_c$ | $R_d$ | $R_1$ | Physical constants [°C.] |
|---|---|---|---|---|---|---|
| 2.23 | H | H | H | 4-OCF$_3$ | SCH(CH$_3$)$_2$ | |
| 2.24 | H | H | H | H | SCH(CH$_3$)$_2$ | oil |
| 2.25 | 2-Cl | H | 4-Cl | H | SCH(CH$_3$)$_2$ | m.p. 119–120° |
| 2.26 | 2-Cl | H | 4-Cl | H | OC(CH$_3$)$_3$ | |
| 2.27 | 2-Cl | H | 4-Cl | H | NHCH(CH$_3$)$_2$ | |
| 2.28 | 2-CH$_3$ | H | 4-CH$_3$ | H | SC(CH$_3$)$_3$ | |
| 2.29 | 2-Cl | H | 4-CH$_3$ | H | SC(CH$_3$)$_3$ | |
| 2.30 | 2-Cl | H | 4-CH$_3$ | H | OCH(CH$_3$)$_2$ | |
| 2.31 | 2-CH$_3$ | H | 4-Cl | H | SCH(CH$_3$)$_2$ | m.p. 109° |
| 2.32 | 2-Br | H | 4-Cl | H | SC(CH$_3$)$_3$ | |
| 2.33 | 2-Br | H | 4-Br | H | OC(CH$_3$)$_3$ | |
| 2.34 | 2-Br | H | 4-Br | H | NHCH(CH$_3$)$_2$ | |
| 2.35 | 2-Br | H | 4-Br | H | SC(CH$_3$)$_3$ | |
| 2.36 | 2-Br | H | 4-Br | H | S—cyclohexyl | |
| 2.37 | 2-F | H | 4-Br | H | SC(CH$_3$)$_3$ | |
| 2.38 | 2-F | H | 4-Br | H | OCH(CH$_3$)C$_2$H$_5$ | |
| 2.39 | 2-F | H | 4-F | H | SCH(CH$_3$)$_2$ | |
| 2.40 | 2-OCHF$_2$ | H | 4-Br | H | SC(CH$_3$)$_3$ | |
| 2.41 | 2-OCHF$_2$ | H | 4-Cl | H | SC(CH$_3$)$_3$ | |
| 2.42 | 2-CH$_3$ | H | 4-Cl | H | SC(CH$_3$)$_3$ | m.p. 137–138° |
| 2.43 | 2-CH$_3$ | H | 4-Cl | H | OC(CH$_3$)$_3$ | |
| 2.44 | 2-CH$_3$ | H | 4-Cl | H | SCH$_2$CH(CH$_3$)$_2$ | |
| 2.45 | 2-OCHF$_2$ | H | 4-F | H | SCH(CH$_3$)$_2$ | |
| 2.46 | 2-Cl | H | 4-Br | H | SC$_4$H$_9$(tert.) | |
| 2.47 | 2-Cl | H | 4-Br | H | SC$_3$H$_7$(iso) | |
| 2.48 | 2-Cl | H | 4-Br | H | S—benzyl | |
| 2.49 | 2-Cl | H | 4-Br | H | OC$_4$H$_9$(tert.) | |
| 2.50 | 2-Cl | H | 4-Cl | H | SC(CH$_3$)$_2$C$_2$H$_5$ | |
| 2.51 | 2-CH$_3$ | H | 4-Cl | H | SC$_4$H$_9$(sec.) | |
| 2.52 | H | H | H | H | NHCH$_3$ | |
| 2.53 | H | H | H | H | NHC$_3$H$_7$(iso) | |
| 2.54 | H | H | H | H | NHC$_4$H$_9$(n) | |
| 2.55 | H | H | H | H | N(CH$_3$)$_2$ | |
| 2.56 | H | H | H | H | OCH$_3$ | |
| 2.57 | H | H | H | H | OC$_3$H$_7$(n) | |
| 2.58 | H | H | H | H | piperidin-1-yl (N—H ring) | |
| 2.59 | H | H | H | H | morpholin-4-yl | |
| 2.60 | H | H | 4-Cl | H | NHC$_2$H$_5$ | |
| 2.61 | H | H | 4-Cl | H | N(CH$_3$)C$_2$H$_5$ | |
| 2.62 | H | H | 4-Cl | H | piperidin-1-yl (N—H ring) | |
| 2.63 | H | H | 4-Cl | H | morpholin-4-yl | |
| 2.64 | H | H | 4-Cl | H | piperazin-1-yl (N—NH) | |

TABLE 2-continued

Compounds of the formula

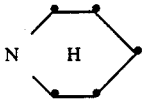

| Comp. No. | $R_a$ | $R_b$ | $R_c$ | $R_d$ | $R_1$ | Physical constants [°C.] |
|---|---|---|---|---|---|---|
| 2.65 | H | H | 3-Cl | 5-Cl | $N(C_2H_5)_2$ | |
| 2.66 | 2-Cl | H | 4-Cl | H | $NHC_3H_7(n)$ | |
| 2.67 | 2-Cl | H | 4-Cl | H | (piperidino, NH) | |
| 2.68 | 2-CH$_3$ | H | 4-Cl | H | (morpholino, N–O) | |

| Formulation Examples (% = percent by weight) | | | |
|---|---|---|---|
| F1. Emulsion concentrates | (a) | (b) | (c) |
| active ingredient from the Tables | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenyl-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| F2. Granulates | (a) | (b) |
|---|---|---|
| active ingredient from the Tables | 5% | 10% |
| kaolin | 94% | — |
| highly dispersed silicic acid | 1% | — |
| attapulgite | — | 90% |

| F3. Wettable powders | (a) | (b) | (c) |
|---|---|---|---|
| active ingredient from the Tables | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. There are thus obtained wettable powders which can be diluted with water to give suspensions of the required concentration.

| F4. Dusts | (a) | (b) |
|---|---|---|
| active ingredient from the Tables | 5% | 8% |
| talcum | 95% | — |
| kaolin | — | 92% |

Dusts ready for use are obtained by mixing the active ingredient with the carriers, and grinding the mixture in a suitable mill.

BIOLOGICAL EXAMPLES

EXAMPLE B1

Action against *Puccinia graminis* on wheat (a) Residual protective action

Six days after being sown, wheat plants are sprayed with a spray liquor prepared from wettable powder of the active ingredient (0.006% of active ingredient). After 24 hours, the treated plants are infested with a uredospore suspension of the fungus. After an incubation time of 48 hours at about 20° C. with 95-100% relative humidity, the infested plants are kept in a greenhouse at about 22° C. An assessment of the development of rust pustules is made 12 days after infestation.

(b) Systemic action

A spray liquor prepared from wettable powder of the active ingredient (0.002% of active ingredient, relative to the volume of soil) is poured onto the soil of wheat plants 5 days after sowing. After 48 hours, the treated plants are infested with a uredospore suspension of the fungus. After an incubation time of 48 hours at about 20° C. with 95-100% relative humidity, the infested plants are kept in a greenhouse at about 22° C. An assessment of the development of rust pustules is made 12 days after infestation.

Compounds from the Tables exhibit a good action against Puccinia fungi. Untreated but infested control plants display a level of Puccinia infection of 100%. Among other effective compounds, the compounds Nos. 1.1–1.4, 1.8, 1.12–1.14, 1.17–1.24, 1.41, 1.88, 1.89, 1.92, 1.95, 1.99–1.111, 1.117, 1.137–1.165, 1.168–1.178, 1.185, 1.187, 1.196–1.226, 2.7, 2.8, 2.11, 2.12, 2.15–2.18, 2.24–2.26, 2.47, 2.57, 75 and 76 reduce Puccina infection to 0 to 5%.

EXAMPLE B2

Action against *Cercospora arachidicola* on groundnut plants (a) Residual-protective action Groundnut plants 10–15 cm in height are sprayed with a spray liquor produced from wettable powder of the active ingredient (0.002% of active ingredient); and 48 hours later they are infested with a conidiospore suspension of the fungus. The infested plants are incubated for 72 hours at about 21° C. with high relative humidity, and are subsequently kept in a greenhouse until the typical leaf spots have appeared. The assessment of the fungicidal action is made 12 days after infestation, and is based on the number and size of the occurring spots.

(b) Systemic action

A spray liquor prepared from wettable powder of the active ingredient (0.06% of active ingredient, relative to the volume of soil) is poured onto the soil of groundnut plants 10–15 cm in height. After 48 hours, the treated plants are infested with a conidiospore suspension of the fungus, and are subsequently incubated for 72 hours at about 21° C. with high relative humidity. The plants are then kept in a greenhouse, and an assessment of the extent of fungus infection is made after 11 days.

Compared to untreated, but infested control plants (number and size of spots =100%), groundnut plants which have been treated with active ingredients from the Tables exhibit a greatly reduced level of Cercospora infection. Thus the compounds Nos. 1.1, 1.3, 1.4, 1.12, 1.23, 1.30, 1.45, 1.99, 2.11, 2.12, 2.15, 2.16, 75 and 76 prevent an occurrence of spots in the above tests almost completely (0–10%).

EXAMPLE B3

Action against *Erysiphe graminis* on barley (a) Residual protective action

Barley plants about 8 cm in height are sprayed with a spray liquor prepared from wettable powder of the active ingredient (0.006% of active ingredient). After 3–4 hours, the treated plants are dusted with conidiospores of the fungus. The infested barley plants are kept in a greenhouse at about 22° C., and the extent of fungus infection is assessed after 10 days.

(b) Systemic action

A spray liquor prepared from wettable powder of the active ingredient (0.002% of active ingredient, relative to the volume of soil) is poured onto the soil of barley plants about 8 cm in height. Care is taken to ensure that the spray liquor does not come into contact with the parts of the plants above the soil. After 48 hours, the treated plants are dusted with conidiospores of the fungus. The infested barley plants are kept in a greenhouse at about 22° C., and an assessment of the extent of fungus infection is made after 10 days.

Compounds of the formula I exhibit a good action against Erysiphe fungus. Untreated but infested control plants display a level of Erysiphe infection of 100%. Among other effective compounds from the Tables, the compounds Nos. 1.1–1.5, 1.7–1.30, 1.45, 1.60, 1.70, 1.88–1.194, 2.1, 2.7, 2.8, 2.11, 2.12, 2.15, 2.16, 2.24, 2.25, 2.31, 2.42, 75, 76, 99, 108e and 114 reduce fungus infection on barley plants to 0 to 5%.

EXAMPLE B4

Residual-protective action against *Venturia inaequalis* on apple shoots

Apple seedlings having 10–20 cm long fresh shoots are sprayed with a spray liquor prepared from wettable powder of the active ingredient (0.06% of active ingredient). The treated plants are sprayed after 24 hours with a conidiospore suspension of the fungus. The plants are then incubated for 5 days with 90–100% relative humidity, and for a further 10 days they are kept at 20–24° C. in a greenhouse. The extent of scab infection is assessed 15 days after infestation.

Compounds from Tables 1 and 2, particularly Comp. 1.3 and 1.12, bring about a clear reduction of infection. Untreated but infested shoots show a 100% level of Venturia infection.

EXAMPLE B5

Action against *Botrytis cinerea* on bean plants

Residual protective action

Bean plants about 10 cm in height are sprayed with a spray liquor prepared from wettable powder of the active ingredient (0.02% of active ingredient). The plants are infested after 48 hours with a conidiospore suspension of the fungus. The extent of fungus infection is assessed after incubation of the infested plants for 3 days at 21° C. with 95–100% relative humidity.

The compounds from Tables 1 and 2 reduce in many cases fungus infection to a great extent. At a concentration of 0.02%, a very effective action is exhibited for example by the compounds from the Tables, thus for example by the compounds Nos. 1.1, 1.3, 1.4, 1.12, 2.11, 2.12, 2.15 and 2.16 (infection 0 to 5%). The Botrytis infection on untreated but infested bean plants is 100%.

What is claimed is:

1. A compound of the formula I $$R_n\text{-}\!\!+\!\!A\!\!+\!\!C=N-\!\!\left\langle\begin{array}{c}=N\\ \\ =N\end{array}\right\rangle \quad (I)$$
$$\phantom{R_n\text{-}\!\!+\!\!A\!\!+\!\!}|\phantom{C=N}$$
$$\phantom{R_n\text{-}\!\!+\!\!A\!\!+\!\!}R_1$$

wherein

A is phenyl, naphthyl, biphenyl, phenoxyphenyl or phenylthiophenyl,

R is halogen, cyano, nitro, $C_1$–$C_4$-alkyl, $C_1$–$C_4$-alkoxycarbonyl, hydroxyl, $C_1$–$C_4$-alkoxy, $C_1$–$C_4$-haloalkoxy, $C_1$–$C_4$-haloalkyl or di($C_1$–$C_4$-alkyl)amino, n is 0, 1, 2, 3, 4 or 5, $R_1$ is one of the groups $OR_2$, $SR_2$ or $N(R_3)(R_4)$, in which $R_2$ is $C_1$–$C_8$-alkyl, $C_3$–$C_8$-alkenyl, $C_3$–$C_8$-alkynyl, or a $C_1$–$C_8$-alkyl group monosubstituted by R, or a radical from the group consisting of phenyl, phenalkyl ($C_1$–$C_4$), $C_3$–$C_7$-cycloalkyl and furfuryl, which is unsubstituted or mono- to trisubstituted by R, and $R_3$ and $R_4$ independently of one another are each hydrogen or $C_1$–$C_4$-alkyl, or when A is phenyl or phenoxyphenyl, $R_3$, and $R_4$, together with the amine nitrogen form a saturated, five- or six-membered heterocycle which contains as hetero atom either just the amine nitrogen or a further hetero atom N, 0 or S.

2. A compound according to claim 1, wherein A is phenyl, naphthyl, biphenyl, phenoxyphenyl or phenylthiophenyl, R is halogen, cyano, nitro, $C_1$-$C_4$-alkyl, $C_1$-$C_4$-alkoxy, $C_1$-$C_4$-haloalkoxy, $C_1$-$C_4$-haloalkyl or di($C_1$-$C_4$-alkyl)amino, n is 0, 1, 2, 3, 4 or 5, $R_1$ is one of the groups $OR_2$, $SR_2$ or $N(R_3(R_4)$, in which $R_2$ is $C_1$-$C_8$-alkyl, $C_3$-$C_8$-alkenyl, $C_3$-$C_8$-alkynyl, or a radical from the group consisting of phenyl, benzyl, $C_3$-$C_7$-cycloalkyl and furfuryl, which is unsubstituted or mono- to trisubstituted by R, and $R_3$ and $R_4$ independently of one another are each hydrogen or $C_1$-$C_4$-alkyl, or together with the amine nitrogen form a saturated, five- or six-membered heterocycle containing as hetero atom either just the amine nitrogen or a further hetero atom.

3. A compound according to claim 1, wherein A is phenyl, R is hydroxyl, halogen, cyano, methyl, ethyl, methoxycarbonyl, ethoxycarbonyl, methoxy, ethoxy, $CF_3$, $C_1$-$C_2$-haloalkoxy, $N(CH_3)_2$ or $N(C_2H_5)_2$, n is 1, 2 or 3, $R_1$ is one of the groups $OR_2$ or $SR_2$, in which $R_2$ is $C_1$-$C_8$-alkyl, $C_3$-$C_8$-alkenyl, $C_3$-$C_8$alkynyl, or a $C_1$-$C_4$-alkyl group which is monosubstituted by hydroxyl, halogen, cyano, methoxycarbonyl, ethoxycarbonyl, methoxy, ethoxy, $N(CH_3)_2$ or $N(C_2H_5)$, or is a radical from the group consisting of phenyl, phenethyl, benzyl, $C_5$-$C_6$-cycloalkyl and furfuryl, which is unsubstituted or mono- to trisubstituted by halogen, cyano, methyl, ethyl, methoxy, ethoxy, $CF_3$, $C_1$-$C_2$-haloalkoxy or $N(C_1$-$C_2$-alkyl)$_2$.

4. A compound according to claim 1, wherein A is phenyl, R is halogen, cyano, methyl, ethyl, methoxy, ethoxy, $CF_3$, $C_1$-$C_2$-haloalkoxy, $N(CH_3)_2$ or $N(C_2H_5)_2$, n is 1, 2 or 3, $R_1$ is one of the groups $OR_2$ or $SR_2$, in which $R_2$ is $C_1$-$C_8$-alkyl, $C_3$-$C_8$-alkenyl, $C_3$-$C_8$-alkynyl, or a radical from the group consisting of phenyl, benzyl, $C_5$-$C_6$-cycloalkyl and furfuryl, which is unsubstituted or mono- to trisubstituted by halogen, cyano, methyl, ethyl, methoxy, ethoxy, $CF_3$, $C_1$-$C_2$-haloalkoxy or $N(C_1$-$C_2$-alkyl)$_2$.

5. A compound according to claim 4, wherein A is phenyl, R is fluorine, chlorine, bromine, methyl, methoxy or $CF_3$, n is 1 or 2, $R_1$ is $OR_2$ or $SR_2$, in which $R_2$ is $C_1$-$C_5$-alkyl, $C_3$-$C_4$-alkenyl, $C_3$-$C_4$-alkynyl, cyclopentyl, cyclohexyl or furfuryl, or is a radical from the group consisting of phenyl and benzyl, which is unsubstituted or mono- to trisubstituted by fluorine, chlorine, bromine, methyl, methoxy or $CF_3$.

6. A compound according to claim 5, wherein R is fluorine or chlorine, n represents the 2- and 4-position of the phenyl ring, $R_1$ is $OR_2$ or $SR_2$, in which $R_2$ is $C_1$-$C_5$-alkyl, allyl, propargyl, cyclohexyl or benzyl, or phenyl which is unsubstituted or mono- to trisubstituted by fluorine, chlorine, bromine, methyl, methoxy or $CF_3$.

7. A compound according to claim 1, wherein A is phenoxyphenyl, and n is 0, 1, 2, 3, 4 or 5, R is hydroxyl, halogen, cyano, methyl, ethyl, methoxycarbonyl, ethoxycarbonyl, methoxy, ethoxy, $CF_3$, $C_1$-$C_2$-haloalkoxy, $N(CH_3)_2$ or $N(C_2H_5)_2$, $R_1$ is one of the groups $OR_2$ or $SR_2$, in which $R_2$ is $C_1$-$C_8$-alkyl, $C_3$-$C_8$-alkenyl, $C_3$-$C_8$-alkynyl, or a $C_1$-$C_4$-alkyl group which is monosubstituted by hydroxyl, halogen, cyano, methoxycarbonyl, ethoxycarbonyl, methoxy, ethoxy, $N(CH_3)_2$ or $N(C_2H_5)$, or is a radical from the group consisting of phenyl, phenethyl, benzyl, $C_5$-$C_6$-cycloalkyl and furfuryl, which is unsubstituted or mono- to trisubstituted by halogen, cyano, methyl, ethyl, methoxy, ethoxy, $CF_3$, $C_1$-$C_2$-haloalkoxy or $N(C_1$-$C_2$-alkyl)$_2$.

8. A compound according to claim 1, wherein A is phenoxyphenyl, R is halogen, cyano, methyl, ethyl, methoxy, ethoxy, $CF_3$, $C_1$-$C_2$-haloalkoxy, $N(CH_3)_2$ or $n(C_2H_5)_2$, n is 0, 1, 2, 3, 4 or 5, $R_1$ is one of the groups $OR_2$ or $SR_2$, in which $R_2$ is $C_1$-$C_8$-alkyl, $C_3$-$C_8$-alkenyl, $C_3$-$C_8$-alkynyl, or a radical from the group consisting of phenyl, benzyl, $C_5$-$C_6$-cycloalkyl and furfuryl, which is unsubstituted or mono- to trisubstituted by halogen, cyano, methyl, ethyl, methoxy, ethoxy, $CF_3$, $C_1$-$C_2$-haloalkoxy or $N(C_1$-$C_2$-alkyl)$_2$.

9. A compound according to claim 8, wherein A is (p-phenoxy)-phenyl.

10. A compound according to claim 9, wherein A is (p-phenoxy)phenyl, R is fluorine, chlorine, bromine, methyl, methoxy or $CF_3$, n is 0, 1, 2, 3 or 4, $R_1$ is $OR_2$ or $SR_2$, in which R is $C_1$-$C_2$-alkyl, $C_3$-$C_4$-alkenyl, $C_3$-$C_4$-alkynyl, cyclopentyl, cyclohexyl, furfuryl, or a radical from the group consisting of phenyl and benzyl, which is unsubstituted or mono- to trisubstituted by fluorine, chlorine, bromine, methyl, methoxy or $CF_3$.

11. A compound according to claim 10, wherein A is (p-phenoxy)phenyl, R is fluorine, chlorine, methyl, methoxy or $CF_3$, n is 0, 1, 2 or 3, $R_1$ is $OR_2$ or $SR_2$, in which $R_2$ is $C_1$-$C_5$-alkyl, allyl, propargyl, cyclohexyl, benzyl, or phenyl which is unsubstituted or mono- to trisubstituted by fluorine, chlorine, bromine, methyl, methoxy or $CF_3$.

12. A compound according to claim 1, wherein A is phenyl or p-phenoxyphenyl, n is 0, 1, 2 or 3, R is halogen, cyano, methyl, ethyl, methoxy, ethoxy, methoxycarbonyl, ethoxycarbonyl, $CF_3$ or $C_1$-$C_2$-haloalkoxy, $R_1$ is the group $N(R_3)$ $(R_4)$, and $R_3$ and $R_4$ independently of one another are each hydrogen or $C_1$-$C_4$-alkyl, or together with the amine nitrogen form a pyrrolidine, piperidine, piperazine or morpholine ring.

13. A compound according to claim 12, wherein R is fluorine, chlorine or methyl.

14. A compound according to claim 1, wherein A is p-biphenyl, n is 0, $R_1$ is either $OR_2$ $SR_2$, and $R_2$ is $C_1$-$C_4$-alkyl, allyl or propargyl.

15. A compound according to claim 1, which is selected from the group consisting of:
5-[2,4-dichlorobenzyl-C-(tert-butylthio)imino]pyrimidine
5-[4-(p-chlorophenoxy)-2-methylbenzyl-C-(tert-butylthio)imino]-pyrimidine,
5-[4-(p-chlorophenoxy)-2-methylbenzyl-C-(iso-propoxy)imino]pyrimidine,
5-[4-(p-chlorophenoxy)-2-chlorobenzyl-C-(tert-butylthio)imino]-pyrimidine,
5-[4-(p-chlorophenoxy)-2-chlorobenzyl-C-(isopropoxy)imino]pyrimidine,
5-[2,4-dichlorobenzyl-C-(isopropoxy)imino]pyrimidine,
5-[2,4-dichlorobenzyl-C-(tert-butoxy)imino]pyrimidine,
5-[2,4-dichlorobenzyl-C-(allyloxy)imino]pyrimidine,
5-[2,4-dichlorobenzyl-C-(n-propoxy)imino]pyrimidine,
5-[4-chlorobenzyl-C-(tert-butylthio)imino]pyrimidine,
5-[2,4-dichlorobenzyl-C-(trifluoroethoxy)imino]pyrimidine,
5-[2,4-dichlorobenzyl-C-(diethylamino)imino]pyrimidine, and
5-[2,4-dichlorobenzyl-C-(tert-butylamino)imino]-pyrimidine.

16. A compound according to claim 1 of the formula

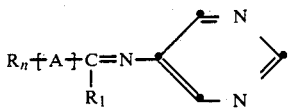

wherein
A is phenyl or phenoxyphenyl,
R is halogen, nitro or $C_1$-$C_4$-alkyl,
n is 1, 2 or 3,
$R_1$ is one of the groups $OR_2$, $SR_2$ or $N(R_3)(R_4)$, in which
$R_2$ is $C_1$-$C_4$-alkyl, $C_3$-alkenyl, phenyl, phenalkyl ($C_1$-$C_4$), $C_3$-$C_5$-cycloalkyl or furfuryl, and
$R_3$ and $R_4$ independently of one another are each hydrogen or $C_1$-$C_4$-alkyl, or together with the amine nitrogen form a saturated, five- or six-membered heterocycle which contains as hetero atom either just the amine nitrogen or a further hetero atom N, 0 or S.

17. A compound according to claim 1 of the formula

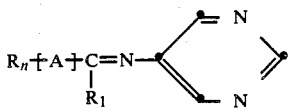

wherein
A is phenyl or phenoxyphenyl;
R is halogen, $C_1$-$C_4$-alkyl, nitro, methoxy or trifluoromethyl;
n is 0, 1 or 2; and
$R_1$ is $C_1$-$C_6$-alkylthio, benzylthio, chlorobenzylthio, chlorobenzyloxy, tolylthio, cyclohexylthio, allylthio, trisethoxy-silanyl-ethylthio, $C_1$-$C_4$-alkoxy, benzyloxy, tolyloxy, cyclohexyloxy, $C_2$-haloalkoxy, allyloxy, propargyloxy, dialkylamino or ethylpiperidine.

18. A composition for controlling or preventing infestation by fungi or bacteria, which composition contains a fungicidally or bactericidally effective amount of at least one compound according to claim 1 and inert carrier.

19. A composition for controlling or preventing infestation by fungi or bacteria, which composition contains a fungicidally or bactericidally effective amount of at least one compound according to claim 2 and inert carrier.

20. A composition for controlling or preventing infestation by fungi or bacteria, which composition contains a fungicidally or bactericidally effective amount of at least one compound according to claim 3 and inert carrier.

21. A composition for controlling or preventing infestation by fungi or bacteria, which composition contains a fungicidally or bactericidally effective amount of at least one compound according to claim 4 and inert carrier.

22. A process for controlling or preventing an infestation of cultivated plants by phytopathogenic fungi or bacteria, which process comprises applying to the plants or to the locus thereof a fungicidally or bactericidally effective amount of a compound claim 1.

23. A method of controlling plant diseases attributable to fungi or bacteria, which method comprises applying a fungicidally or bactericidally effective amount of a compound of claim 1 to a cultivated plant or locus thereof.

24. A method of controlling plant diseases attributable to fungi or bacteria, which method comprises applying to a cultivated plant or locus thereof a fungicidally or bactericidal effective amount of a compound of claim 4.

25. A method according to claim 23, wherein the fungi or bacteria are phytopathogenic fungi.

26. A compound of the formula II

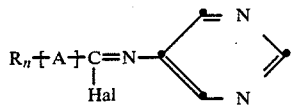

(II)

wherein $R_n$ and A have the meanings defined in claim 1, and Hal is halogen.

* * * * *